US012636514B2

(12) United States Patent
Johnson et al.

(10) Patent No.: US 12,636,514 B2
(45) Date of Patent: May 26, 2026

(54) SYSTEMS AND METHODS FOR PRESERVING AND/OR ENHANCING RESPIRATORY FUNCTION

(71) Applicant: MULTI RADIANCE MEDICAL, Solon, OH (US)

(72) Inventors: Douglas Johnson, Flat Rock, MI (US); Max Kanarsky, Solon, OH (US); Ernesto Cesar Pinto Leal Junior, Sao Paulo (BR)

(73) Assignee: MEDICAL QUANT USA INC., Solon, OH (US)

( * ) Notice: Subject to any disclaimer, the term of this patent is extended or adjusted under 35 U.S.C. 154(b) by 827 days.

(21) Appl. No.: 17/977,413

(22) Filed: Oct. 31, 2022

(65) Prior Publication Data

US 2023/0063704 A1 Mar. 2, 2023

Related U.S. Application Data

(63) Continuation-in-part of application No. PCT/US2021/029131, filed on Apr. 26, 2021.

(Continued)

(51) Int. Cl.
*A61N 5/06* (2006.01)
*A61N 2/00* (2006.01)
(Continued)

(52) U.S. Cl.
CPC ........... *A61N 5/0613* (2013.01); *A61N 5/067* (2021.08); *A61N 2005/0651* (2013.01); *A61N 2005/0659* (2013.01); *A61N 2005/0662* (2013.01)

(58) Field of Classification Search
CPC .. A61N 2/002; A61N 2/06; A61N 2005/0626; A61N 2005/0642;
(Continued)

(56) References Cited

U.S. PATENT DOCUMENTS

2002/0188332 A1* 12/2002 Lurie ................. A61N 1/39044
607/48
2014/0288351 A1 9/2014 Jones
(Continued)

FOREIGN PATENT DOCUMENTS

WO WO-2019165302 A1 * 8/2019 ........... A61B 5/4848
WO 2019227150 A1 12/2019

OTHER PUBLICATIONS

International Search Report and Written Opinion dated Aug. 3, 2021, for corresponding International Application No. PCT/US2021/029131.

*Primary Examiner* — Benjamin J Klein
*Assistant Examiner* — Vynn V Huh
(74) *Attorney, Agent, or Firm* — Tarolli, Sundheim, Covell & Tummino LLP

(57) ABSTRACT

Respiratory function can be preserved and/or enhanced in patients with a respiratory insufficiency using a photoceutical applied by a photoceutical medical device to at least one primary inspiratory muscle and/or a lung. At least one site on a body of a patient can be selected for delivery of the photoceutical to the muscle(s); and the photoceutical can be applied at the at least one site by the photoceutical medical device for a time period from a first start time to a first end time to treat the at least one primary inspiratory muscle and/or the lung of the patient to preserve and/or enhance the respiratory function. The photoceutical can include a light signal with at least one delivery scheme (e.g., superpulsed, pulsed. and/or continuous) and one or more wavelengths.

13 Claims, 12 Drawing Sheets

104

102

Related U.S. Application Data

(60) Provisional application No. 63/017,267, filed on Apr. 29, 2020.

(51) Int. Cl.
*A61N 2/06* (2006.01)
*A61N 5/067* (2006.01)

(58) Field of Classification Search
CPC .... A61N 2005/0644; A61N 2005/0651; A61N 2005/0659; A61N 2005/0662; A61N 5/0613; A61N 5/067
USPC ..................................................... 607/88–94
See application file for complete search history.

(56) References Cited

U.S. PATENT DOCUMENTS

2017/0128736 A1* 5/2017 Johnson ............... A61N 5/0613
2019/0134394 A1 5/2019 O'Mahony

* cited by examiner

104

102

102

| 204 CONTROLLER |
| 202 |

MOTOR    208

CIRCUIT BOARD

206

POWER SOURCE

SYSTEMS AND METHODS FOR PRESERVING AND/OR ENHANCING RESPIRATORY FUNCTION

CROSS-REFERENCE TO RELATED APPLICATIONS

This application has entered the U.S. as a bypass CIP of WO 2021/221851 and claims the benefit of U.S. Provisional Application No. 63/017,267, filed Apr. 29, 2020, entitled "PHOTOBIOMODULATION THERAPY TO INCREASE HEALTH STATUS OF COVID-19 PATIENTS"; U.S. Provisional Application No. 63/035,943, filed Jun. 8, 2020, entitled "PHOTOBIOMODULATION THERAPY TO INCREASE HEALTH STATUS OF COVID-19 PATIENTS"; and U.S. Provisional Application No. 63/115, 158, filed Nov. 18, 2020, entitled "PHOTOBIOMODULA-TION THERAPY TO INCREASE HEALTH STATUS OF COVID-19 PATIENTS". These provisional applications are hereby incorporated by reference in their entirety for all purposes.

TECHNICAL FIELD

The present disclosure relates generally to respiratory function and, more specifically, to systems and methods for preserving and/or enhancing respiratory function in patients at risk of or suffering from respiratory insufficiency through application of a photoceutical through a photoceutical delivery device.

BACKGROUND

A patient's respiratory system performs a respiratory function of gas exchange, which allows the patient's body to receive oxygen from air while clearing waste gasses like carbon dioxide. When a patient's respiratory system struggles to perform gas exchange, the patient suffers from respiratory insufficiency. For example, patients with any type of injury or illness that can affect the respiratory system may suffer from respiratory insufficiency. One type of respiratory insufficiency is acute respiratory distress syndrome (ARDS). ARDS is a life threatening condition where breathing becomes difficult, causing gas exchange to suffer. With ARDS, tissues cannot be oxygenated properly tissues, metabolic processes cannot function efficiently, which causes cellular functions to falter. The symptoms of ARDS are usually shortness of breath, as well as low blood oxygen, rapid breathing, and/or clicking, bubbling, or rattling sounds in the lungs when breathing. ARDS occurs when the millions of alveoli (tiny air sacks of the lungs) fill with excess fluid, causing the breakdown of surfactant, a foamy substance that keeps the lungs fully expanded to enable breathing. Accordingly, with ARDS, breathing becomes difficult and gas exchange cannot occur due to the inability of the lungs to fill with air.

SUMMARY

The present disclosure relates to preserving and/or enhancing respiratory function in patients at risk of or suffering from respiratory insufficiency through application of a photoceutical through a photoceutical delivery device.

In one aspect, the present disclosure can include a method for preserving and/or enhancing respiratory function. At least one site on a body of a patient can be selected for delivery of a photoceutical to at least one primary inspiratory muscle and/or a lung of the patient by a photoceutical medical device. The photoceutical can include light of at least one wavelength. The photoceutical can be applied at the at least one site on the body of the patient by the photoceutical medical device for a time period from a first start time to a first end time to treat the at least one primary inspiratory muscle and/or lung of the patient to preserve and/or enhance a respiratory function of the patient.

In another aspect, the present disclosure can include a photoceutical medical device that can act as the photoceutical delivery device. The device can include a circuit board that includes: a plurality of light sources to provide a light signal and at least two magnets to provide a magnetic signal; the circuit board can also interface with a power source. The plurality of light sources can include at least one superpulsed laser to provide superpulsed light of a first wavelength, at least two non-coherent light sources to provide pulsed and/or continuous light of a second wavelength, and at least two other non-coherent light sources to provide pulsed and/or continuous light of a third wavelength. The photoceutical includes the light signal and the magnetic signal, and is delivered to at least one site on a body of a patient to treat at least one primary inspiratory muscle and/or lung of the patient to preserve and/or enhance a respiratory function of the patient. The light signal includes the superpulsed light of the first wavelength, the pulsed and/or continuous light of the second wavelength, and the pulsed and/or continuous light of the third wavelength.

The photoceutical can be delivered to a patient (e.g., the photoceutical can be configured with one or more parameters) to help the patient achieve goals at various medical stages. For example, delivery of the photoceutical can be used to protect the patient (e.g., before a ventilator is applied) with the goal of helping to reduce the risk of using/requiring a ventilator. As another example, the photoceutical can be delivered during ventilation (e.g., using a ventilator) with the goal of reducing diaphragm dysfunction (during or after ventilation, making it easier to remove the patient from the ventilator). As a further example, the photoceutical can be used after discharge (e.g., from a medical facility) with the goal of improving respiratory function and recovery. In yet another example, the photoceutical can be used after ventilation (e.g., after a patient has been removed from a ventilator) with the goal of improving respiratory function. Additional uses/protections are possible. The delivery can be before hospitalization, during hospitalization, and/or after hospitalization. The deliver can be used without requiring hospitalization (e.g., as a treatment).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
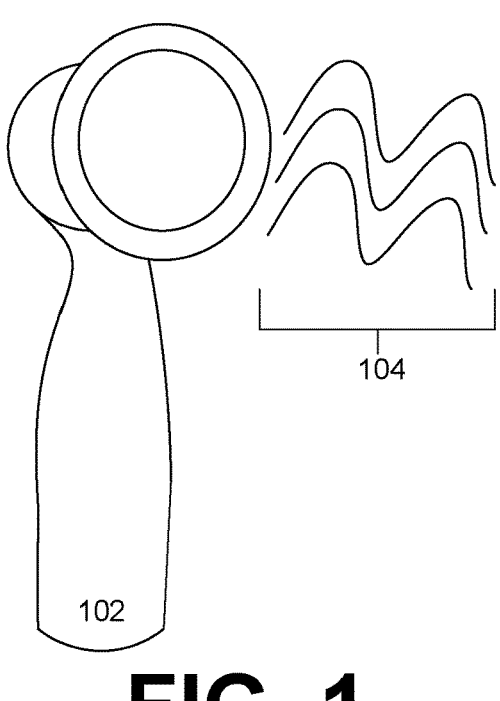
FIG. 1 is a diagram showing an example of a system including a photoceutical medical device that delivers a photoceutical to at least one predefined location on the body of a patient at risk of or suffering from respiratory insufficiency in accordance with an aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "respiratory function" refers to gas exchange performed by a patient's respiratory system.

As used herein, the term "gas exchange" refers to receiving oxygen to be used by a patient's body from air while clearing waste gasses, like carbon dioxide, from the patient's body.

As used herein, the term "respiratory insufficiency" refers to a state when a patient's respiratory system struggles to perform any portion of a gas exchange process. For example, with respiratory insufficiency, a patient's lungs may become unable to take in sufficient oxygen or expel sufficient carbon dioxide, reducing the patient's ability to perform gas exchange to meet the needs of cells in the body. Patients suffering from any type of injury or illness affecting the lung can suffer from respiratory insufficiency, including but not limited to: COVID-19, Duchenne muscular dystrophy (DMD), pneumonia, tuberculosis, sarcoidosis, idiopathic pulmonary fibrosis, interstitial lung disease, lung cancer, pulmonary fibrosis, rheumatoid arthritis, infant respiratory distress syndrome, acute respiratory distress syndrome, inflammatory bowel disease, systemic lupus, asthma, chronic bronchitis, emphysema, cystic fibrosis, pleural effusion, chronic obstructive pulmonary disease (COPD), or the like.

As used herein, the term "photoceutical" refers to a light signal (or a light signal and magnetic signal) used to change a function of at least a portion of a patient's body (e.g., by photobiomodulation to induce a phototherapeutic response using a drug-free, non-invasive treatment procedure). For example, the light signal of the photoceutical may include a combination of a plurality of light signals from a plurality of light sources, each of the plurality of light signals may have a different wavelength, frequency, or other property. The combination of the different properties (like wavelength, for example) can create a synergistic effect.

As used herein, the terms "photoceutical delivery device", "photoceutical medical device", "photoceutical device", and the like, refer to a device configured to apply the photoceutical as a therapeutic agent. For example, the photoceutical delivery device can house the plurality of light sources (and, in some instances, the magnets) to deliver the pharmaceutical. The light sources can include one or more super pulsed lasers, one or more light emitting diodes, one or more infrared light emitting diodes, or the like. For example, the photoceutical medical device can be a probe, a pad, a flexible device, or the like.

As used herein, the term "super pulsed laser" refers to a light source that produces a wavelength of light at a high peak power for a very brief duration. Even though the pulse peaks at a high power level, there are no thermal effects in the tissue. The peak power is high compared to the average output power. By using a super pulsed laser, one is able to more effectively deliver higher densities of light energy into the tissue without associated deleterious thermal effects.

As used herein, the term "incline" refers to a deviation from vertical or horizontal by a certain slope at a particular angle.

As used herein, the term "circuit board" refers to a mechanism to mechanically support and electrically connect electrical components (like light delivery devices) using conductive tracks, pads, and other features etched from one or more sheet layers of a conductive material (like copper) laminated onto and/or between sheet layers of a non-conductive substrate. The circuit board can be rigid and/or flexible. An example of a circuit board can include a printed circuit board.

As used herein, the term "sufficient" refers to an amount adequate enough to satisfy a condition.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

When a patient suffers an injury or disease affecting the respiratory system, the patient can be at risk for respiratory insufficiency or may already suffer from respiratory insufficiency. Such diseases affecting the respiratory system can include, for example, COVID-19, Duchenne muscular dystrophy (DMD), pneumonia, tuberculosis, sarcoidosis, idiopathic pulmonary fibrosis, interstitial lung disease, lung cancer, pulmonary fibrosis, rheumatoid arthritis, infant respiratory distress syndrome, acute respiratory distress syndrome, inflammatory bowel disease, systemic lupus, asthma, chronic bronchitis, emphysema, cystic fibrosis, pleural effusion, chronic obstructive pulmonary disease (COPD), or the like. Respiratory insufficiency can occur when the respiratory system struggles to perform the respiratory function of gas exchange (receiving oxygen from air while clearing waste gasses like carbon dioxide). For example, one type of respiratory insufficiency is acute respiratory distress syndrome (ARDS), where the patient's lungs cannot fill properly with air because of fluid building up inside the alveoli and break down of surfactant, thus preventing adequate amounts of oxygen from moving into the bloodstream and throughout the body, eventually causing respiratory failure due to hypoxemia.

A patient at risk of suffering from or already suffering from respiratory insufficiency risks hospital admission, treatment in the intensive care unit, or even death. To preserve and/or enhance respiratory function in a patient at risk of or suffering from respiratory insufficiency, a photoceutical can be applied to one or more spots on a patient's body through a photoceutical delivery device. For example, the one or more spots on a patient's body can include at least a portion of a diaphragm, one or more intercostal muscles, one or more neck muscles, one or more accessory muscles, and or the lung itself. The diaphragm is a thin dome-shaped muscle situated in the superior aspect of the abdominal cavity below the ribs and the intercostal muscles separating the abdominal cavity from the thoracic cavity. The diaphragm is the major muscle responsible for breathing, working like a piston to expand the chest cavity. During inhalation, the diaphragm contracts, so that its center moves caudally (downward) and its edges move cranially (upward). This compresses the abdominal cavity, raises the ribs upward and outward and thus expands the thoracic cavity. This expansion creates a vacuum that draws air into the lungs. When the diaphragm relaxes, elastic recoil of the thoracic wall causes the thoracic cavity to contract, forcing air out of the lungs, and returning to its dome-shape. Intercostal muscles participate in both inspiration and expiration. The thoracic accessory muscles (scalenes, sternocleidomastoids, pectoralis minor, and erector spinae) all elevate the ribs and facilitate inspiration. The abdominal accessory muscles (rectus abdominis, transverse abdominis, and the obliques) facilitate expiration. The term accessory muscles refers to those muscles that assist, but do not play a primary role, in breathing. Use of these while at rest is often interpreted as a sign of respiratory distress.

Applying a photoceutical to one or more spots on a patient's body (e.g., delivering the photoceutical to the diaphragm, the lung, and/or the neck) can preserve and/or enhance respiratory function. The photoceutical can include a light signal made up of one or more wavelengths from 600 nm-1200 nm. As an example, when three wavelengths are used, two of the wavelengths can be substantially matched and one wavelength different. For instance, the photoceutical can include application of the light signal to each of the one or more spots for a time period. The photoceutical can be delivered by a photoceutical medical device that includes at least one super pulsed laser to provide superpulsed light of the first wavelength, at least two non-coherent light sources to provide light of the second wavelength, and at least two other non-coherent light sources to provide light of a third wavelength (and may, additionally, include one or more magnets to provide a magnetic signal).

The photoceutical can be delivered to a patient (e.g., the photoceutical can be configured with one or more parameters) to help the patient achieve goals at various medical stages. For example, delivery of the photoceutical can be used to protect the patient (e.g., before a ventilator is applied) with the goal of helping to reduce the risk of using/requiring a ventilator. As another example, the photoceutical can be delivered during ventilation (e.g., using a ventilator) with the goal of reducing diaphragm dysfunction (during or after ventilation, making it easier to remove the patient from the ventilator). As a further example, the photoceutical can be used after discharge (e.g., from a medical facility) with the goal of improving respiratory function and recovery. In yet another example, the photoceutical can be used after ventilation (e.g., after a patient has been removed from a ventilator) with the goal of improving respiratory function. Additional uses/protections are possible. The delivery can be before hospitalization, during hospitalization, and/or after hospitalization. The deliver can be used without requiring hospitalization (e.g., as a treatment).

III. Photobiomodulation Therapy (PBMT)

Applying the photoceutical to a patient is a drug-free and non-invasive photobiomodulation therapy (PBMT) that can be used to preserve and/or enhance respiratory function in patients at risk of or suffering from respiratory insufficiency. Examples of such patients include, but are not limited to, patients suffering from COVID-19, Duchenne muscular dystrophy (DMD), pneumonia, tuberculosis, sarcoidosis, idiopathic pulmonary fibrosis, interstitial lung disease, lung cancer, pulmonary fibrosis, rheumatoid arthritis, infant respiratory distress syndrome, acute respiratory distress syndrome, inflammatory bowel disease, systemic lupus, asthma, chronic bronchitis, emphysema, cystic fibrosis, pleural effusion, chronic obstructive pulmonary disease (COPD), or the like.

In some instances, respiratory function can be preserved and/or enhanced by treating muscles needed for breathing, the primary inspiratory muscles including the diaphragm, intercostals, and accessory chest or neck muscles, other muscles, and/or the patient's lungs. Application of a dose of the photoceutical to a patient can induce a phototherapeutic response that can, for example, increase muscle thickness, reduce dysfunction, fatigue, and weakening of muscles needed for breathing. by preserving respiratory function by minimizing muscle weakness and fatigue in the primary inspiratory muscles. The preserved and/or enhanced respiratory function can cause improved blood oxygenation, improved tissue oxygenation, improved cytoprotection, ventilation/perfusion, immune response and/or overall function of the immune system, decreased inflammation, reduced acute respiratory distress syndrome, maintained muscle morphology, maintained muscle function, reduced infection, reduced inflammation, reduced sepsis, and/or decreased length of hospitalization if admitted to the hospital. In fact, the preservation of muscular function may trigger a cascade of positive effects in the patient. In other instances, respiratory function can be preserved by treating the lung itself and/or muscles surrounding the lung.

The light signal of the photoceutical may be one light signal (wavelength 600-1200 nm), but may also include a combination of a plurality of light signals from a plurality of light sources, each of the plurality of light signals may have a different wavelength (independently from 600-1200 nm), frequency, or other property. The combination of the different properties (like wavelength, for example) can create a synergistic effect. The light signal includes a combination of a superpulsed light of a first wavelength (850 nm-950 nm), light of a second wavelength (800 nm-900 nm), and light of a third wavelength (580 nm-800 nm). In some instances, the light signal includes a magnetic signal (or magnetic field). A dose of the light signal can be applied for a time period from a first time to a second time, wherein the time periods is between 30 seconds to 300 seconds to each predefined site on the patient's body for treatment of the diaphragm, the primary inspiratory muscles including the diaphragm, intercostals, and accessory muscles. In some instances, the photoceutical can encourage greater oxygen uptake and/or photodissociation of oxygen by hemoglobin cells.

The light of PBMT has been shown to have a modulatory effect based on the principle that certain molecules in living systems absorb photons and trigger signalling pathways in response to light. When a photon of light is absorbed by a chromophore in a cell, an electron in the chromophore can become excited and jump from a low-energy orbit to a higher-energy orbit. This stored energy then can be used by the living system to perform various cellular tasks, such as cellular metabolism, microcirculation, promoting oxygen availability, and modulation of the inflammatory process, attributable to the acceleration of the electron transport chain and reestablishment of oxidative phosphorylation. While not wishing to be bound by theory, there is strong evidence to suggest that one of the basics of PBMT is the acceleration of electron transfer by electromagnetic radiation in the visible and near infrared region of the spectrum, via the modulation of cytochrome c-oxidase ("CCO") activity in muscle cells. CCO is the primary photo acceptor of visible to near infrared light energy and is the enzyme responsible for catalysing oxygen consumption in cellular respiration and for the production of nitric oxide under hypoxic conditions. High-energy electrons are passed from electron carriers through a series of trans-membrane complexes (including CCO) to the final electron acceptor, generating a proton gradient that is used to produce adenosine triphosphate (ATP). The application of light directly results in ATP production and electron transport. In short, the application of PBMT can increase ATP production, down-regulate cellular respiration modulated by NO, and promotes the metabolism of oxygen, while increasing the production of reactive oxygen species (ROS).

Additionally, in the example where super pulsed light is used, transcutaneous irradiation with super pulsed light can directly affect the release of nitric oxide from hemoglobin and nitrosylated myoglobin or the production by NO synthase causing vasodilatation, increasing blood flow, and increasing oxygen availability to the tissues. Furthermore, the super pulsed light irradiation has been shown to have modulatory effects on inflammatory response though modulation of inflammatory cell migration, a dual-effect on cytokines through decreased release of pro-inflammatory cytokines and increased release of anti-inflammatory cytokines. Furthermore, an improvement on airway reactivity dysfunction is achieved by simultaneously reducing both TNF-α and isoform of NO synthase (iNOS). Finally, there is evidence that the effects in attenuating the lung inflammation is driven to restore the balance between the pro- and antioxidants mediators, which can be helpful in the overall improvement of health status.

IV. Systems

As shown in FIG. 1, one aspect of the present disclosure can include a system including a photoceutical medical device 102 that generates and delivers a photoceutical 104. Even though the photoceutical medical device 102 is illustrated as a probe, it will be understood that the photoceutical medical device 102 can take other forms, like a pad, a flexible device, or the like. The system can be used to deliver the photoceutical 104 to at least one predefined location (or site) on the body of a patient at risk for respiratory insufficiency or may already suffer from respiratory insufficiency. Such a patient may suffer from an injury or disease affecting the respiratory system, such as COVID-19, Duchenne muscular dystrophy (DMD), pneumonia, tuberculosis, sarcoidosis, idiopathic pulmonary fibrosis, interstitial lung disease, lung cancer, pulmonary fibrosis, rheumatoid arthritis, infant respiratory distress syndrome, acute respiratory distress syndrome, inflammatory bowel disease, systemic lupus, asthma, chronic bronchitis, emphysema, cystic fibrosis, pleural effusion, chronic obstructive pulmonary disease (COPD), or the like. The photoceutical can be delivered to a patient (e.g., the photoceutical can be configured with one or more parameters) to help the patient achieve goals at various medical stages. For example, delivery of the photoceutical can be used to protect the patient (e.g., before a ventilator is applied) with the goal of helping to reduce the risk of using/requiring a ventilator. As another example, the photoceutical can be delivered during ventilation (e.g., using a ventilator) with the goal of reducing diaphragm dysfunction (during or after ventilation, making it easier to remove the patient from the ventilator). As a further example, the photoceutical can be used after discharge (e.g., from a medical facility) with the goal of improving respiratory function and recovery. In yet another example, the photoceutical can be used after ventilation (e.g., after a patient has been removed from a ventilator) with the goal of improving respiratory function. Additional uses/protections are possible. The delivery can be before hospitalization, during hospitalization, and/or after hospitalization. The deliver can be used without requiring hospitalization (e.g., as a treatment).

Figure 7:
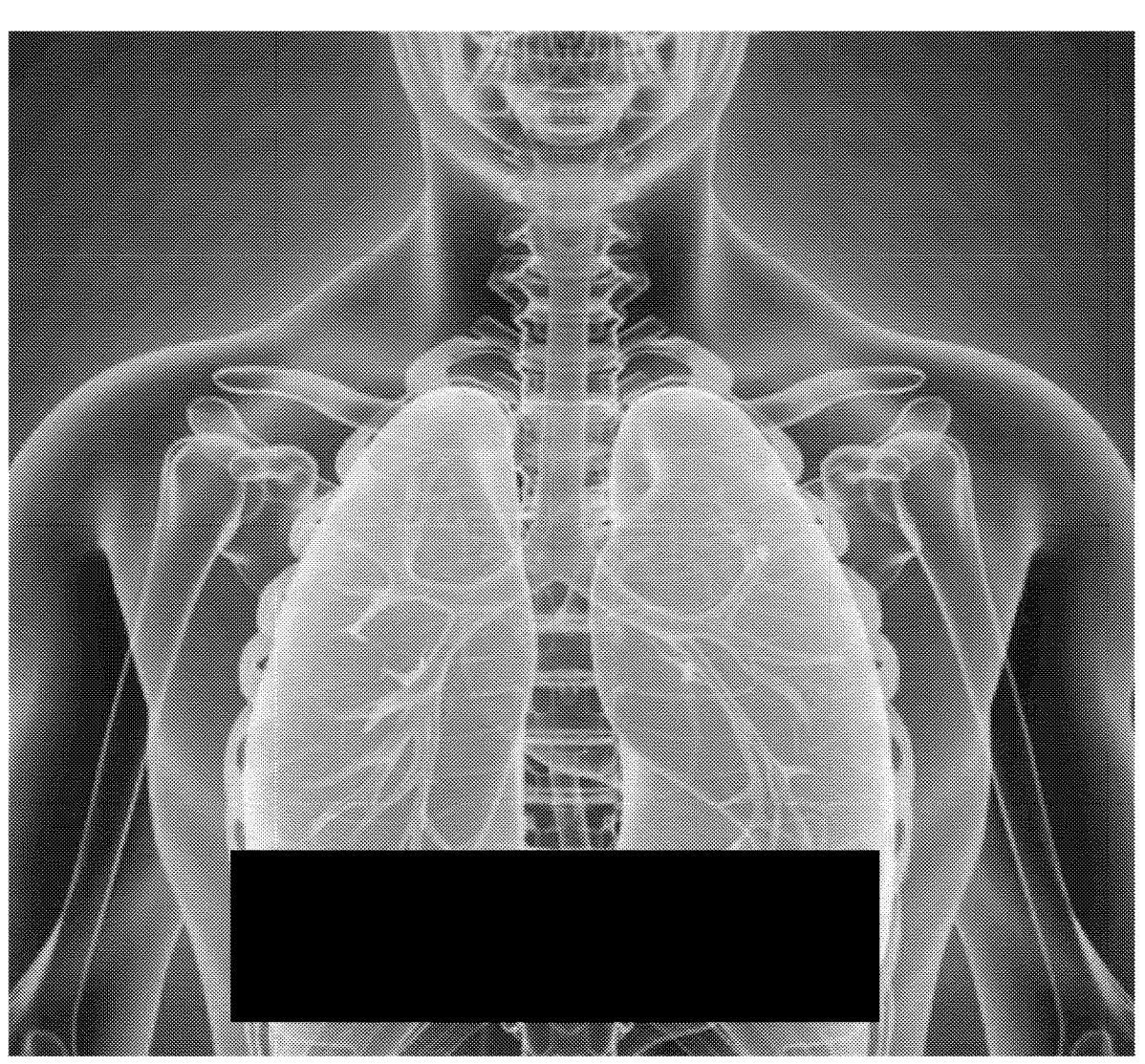
FIGS. 7-9 show examples of where the site(s) can be located (the site(s) can include one or more locations from FIGS. 7-9)
Figure 8:
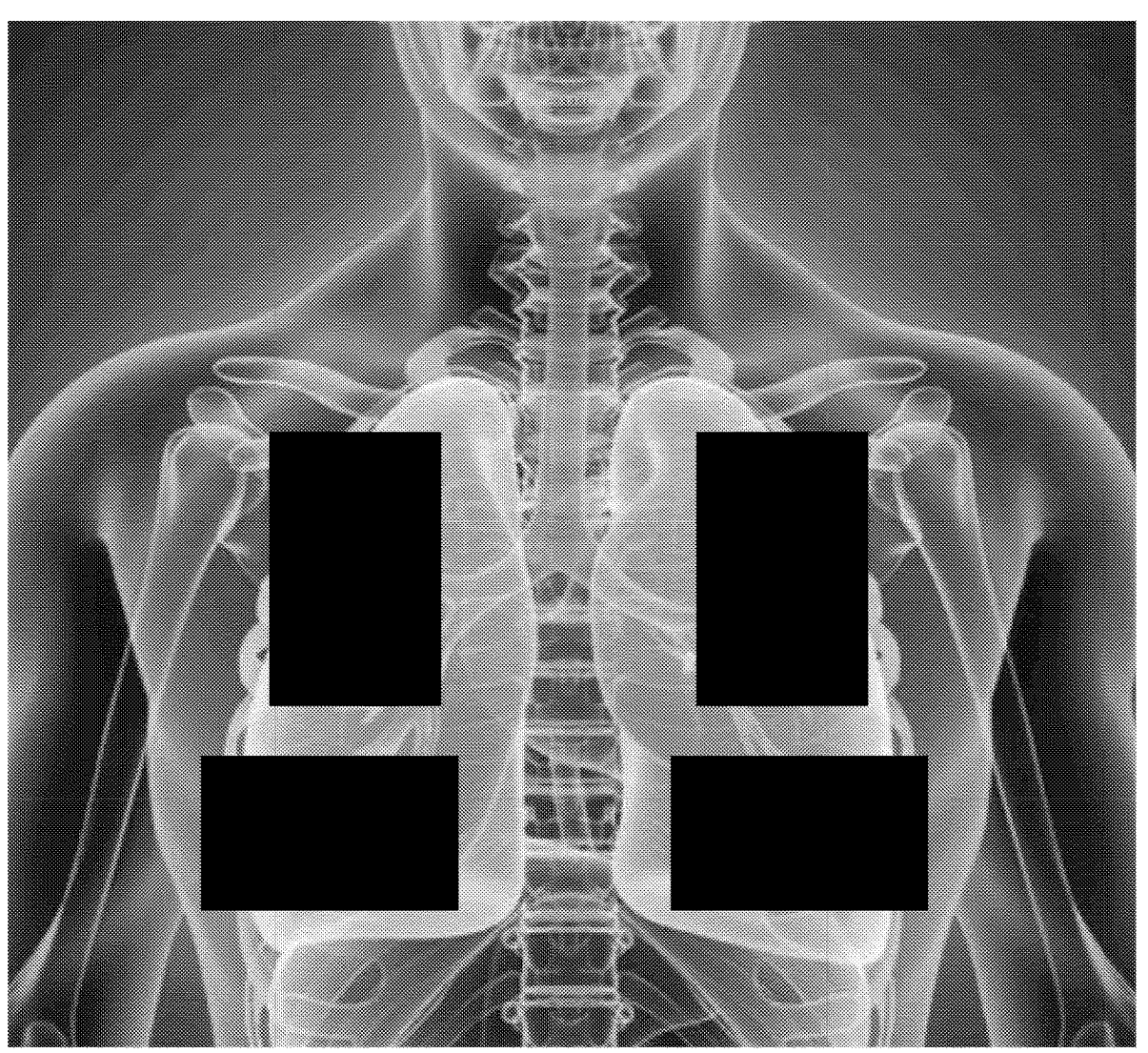
Figure 9:
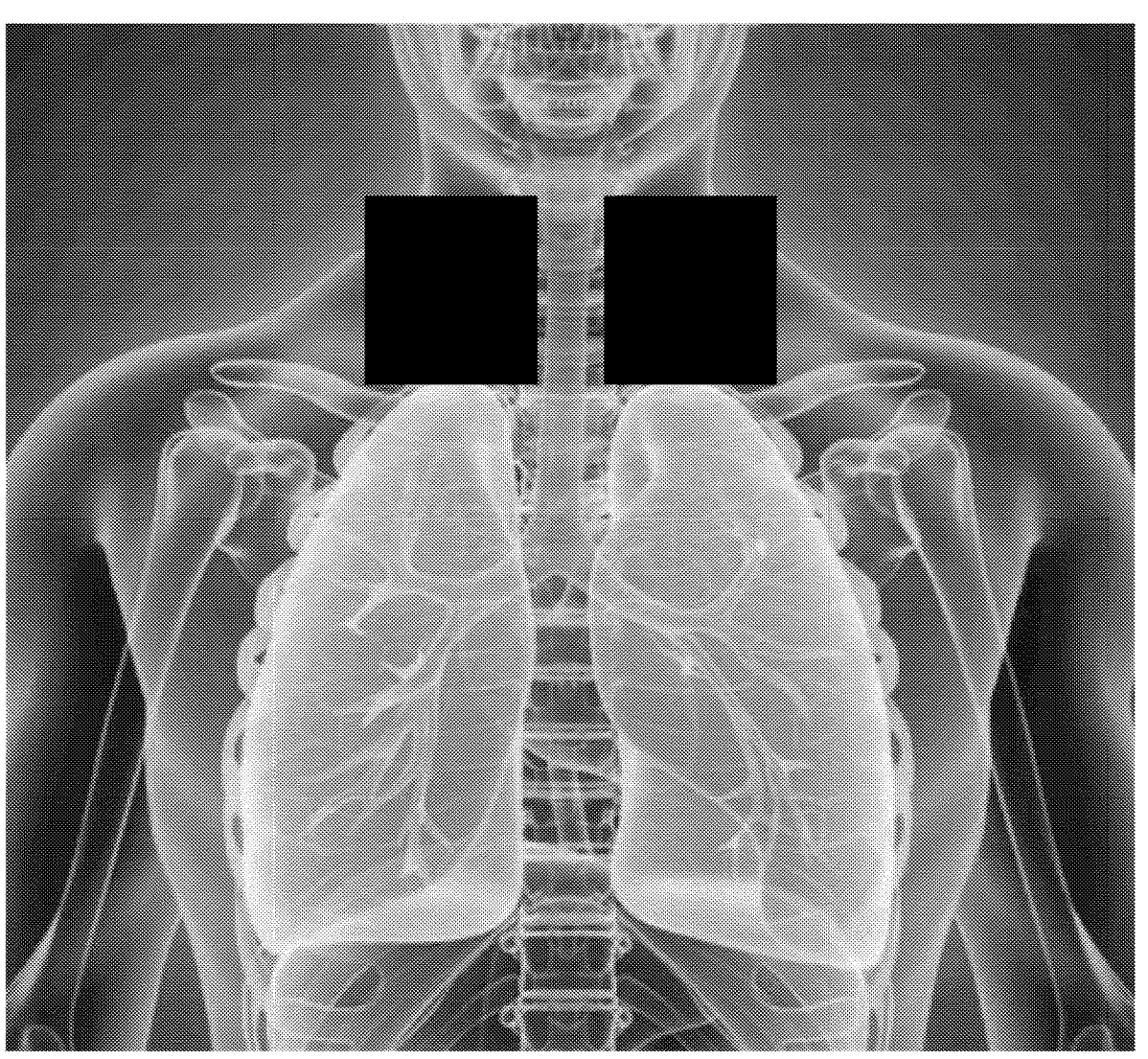

As noted, the photoceutical medical device 102 can be used to deliver the photoceutical 104 to at least one predefined location (or site) on the body of the patient (the predefined locations are shown in FIGS. 7-9, note that one or more sites can be chosen from the locations within the black boxes illustrated in FIGS. 7-9). The location/site can be covering at least a portion of the patient's primary inspiratory muscles, such as the diaphragm, the neck muscles, the intercostal muscles, the accessory muscles, or the like. However, the site may also facilitate delivery of the photoceutical to at least one of the patient's lungs. Applying the photoceutical to the at least one site can improve the function and strength of the muscles, which can preserve respiratory function, improve blood oxygenation, tissue oxygenation, and immune response, decrease inflammation and infection/sepsis, reduce acute respiratory distress syndrome and other instances or respiratory insufficiency, and/or maintain muscle morphology/function. In some instances, the photoceutical is delivered to at least two sites on the patient's body. In other instances, the photoceutical is delivered to a plurality of sites on the patient's body. As an example, the at least two sites can include at least two sites targeting the patient's diaphragm and at least one site on the patient's neck (targeting at least the sternocleidomastoid muscle(s), and/or the scalene muscle(s)). In other instances, the at least two sites on a patient's body can include from 1 to 3 sites (bilaterally) targeting the patient's diaphragm and from 0-1 site (bilaterally) targeting the patient's neck (targeting at least the sternocleidomastoid muscle(s), and/or the scalene muscle(s)). As another example, the at least two sites can include sites on the patient's chest, around the lungs (e.g., at least one target aiming for the top of the lungs and/or at least one target aiming for the bottom of the lungs).

The photoceutical 104 can include a light signal. The light signal, in some instances, can include a single wavelength of light. The single wavelength can be a value selected between 600 nm and 1200 nm. In other instances, the light signal can include multiple wavelengths of light. The multiple wavelengths can independently be values selected between 600 nm and 1200 nm.

In some instances, the light signal can include a single wavelength of light (e.g., red light between 600-700 nm). However, in other instances, the light signal can be made up of a combination of different lights from different sources. For example, the different lights can be coherent or incoherent and have different wavelengths, frequencies, energies, energy density delivered, and the like. In one instance, the light signal can include superpulsed light of a first wavelength and at least one of light of a second wavelength and/or light of a third wavelength. In another instance, the light signal can include superpulsed light of a first wavelength, light of a second wavelength, and light of a third wavelength (two of the wavelengths can be substantially matched and one wavelength different). For example, the first wavelength can be between 850 nm and 950 nm, the second wavelength can be between 800 nm and 900 nm, and the third wavelength can be between 580 nm and 800 nm. In some instances, the photoceutical 104 can also include a magnetic signal (e.g., from one or more magnetic sources, which can be permanent magnets, with a magnetism provided by each magnetic source of from 0.01 mT-100 mT).

The photoceutical medical device 102 can deliver a total dose of energy (based on the individual doses delivered by each of the light sources) to each of the at least one predefined locations on the body of a patient. The total dose of energy can be from 3 J-2000 J, for example, 31.5 J. The photoceutical 104 can be applied to each predefined site for a time period from a first start time to a first end time to treat the at least one primary inspiratory muscle of the patient to preserve and/or enhance a respiratory function of the patient, wherein the time period is between 30 seconds to 1 hour (may be the same or variable for different locations).

The photoceutical 104 can be delivered to at least one predefined location on the body of the patient by the photoceutical medical device 102. The photoceutical medical device 102 can include at least one super pulsed laser to provide superpulsed light of the first wavelength and at least two non-coherent light sources to provide light of the second wavelength and/or at least two other non-coherent light sources to provide light of a third wavelength. The photoceutical medical device 102 can also include at least two magnetic sources to provide the magnetic field. However, in some instances, the photoceutical medical device 102 can include at least four super pulsed lasers to provide superpulsed light of the first wavelength and at least eight non-coherent light sources to provide light of the second wavelength and/or at least eight other non-coherent light sources to provide light of a third wavelength. In these instances, the photoceutical medical device 102 can also include at least eight magnetic sources to provide the magnetic field.

Figure 2:
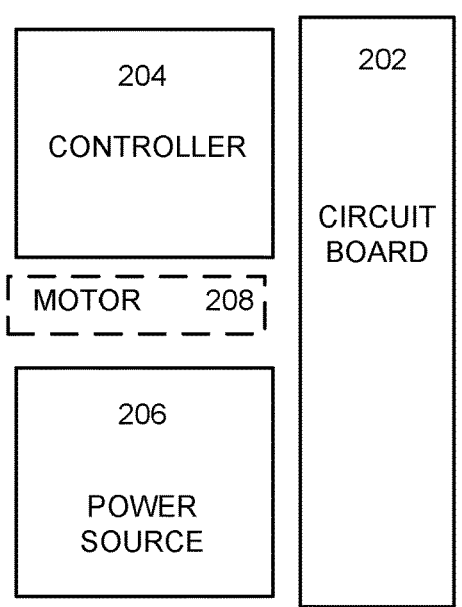
FIG. 2 is a diagram showing an example interior of the photoceutical medical device of FIG. 1.

The photoceutical medical device 102 can be of different shapes and sizes as long as the photoceutical medical device is shaped and sized to deliver the photoceutical 104 to the one or more predefined sites on the patient. As examples, the photoceutical medical device 102 may be configured to be held against (as illustrated) and/or placed onto one or more treatment sites for delivery of the photoceutical 104. While the photoceutical 104 can be emitted from a one or more circular emitters (as shown in FIG. 1), the emitters need not be circular. For example, the emitters can be one or more diamonds, crosses, squares, rectangles, or the like. Components of the photoceutical medical device 102 that facilitate generation and delivery of the photoceutical 104 are shown in FIG. 2. It should be understood that the photoceutical medical device 102 can include additional components to facilitate the generation and delivery of the photoceutical 104 (e.g., one or more lenses).

Figure 5:
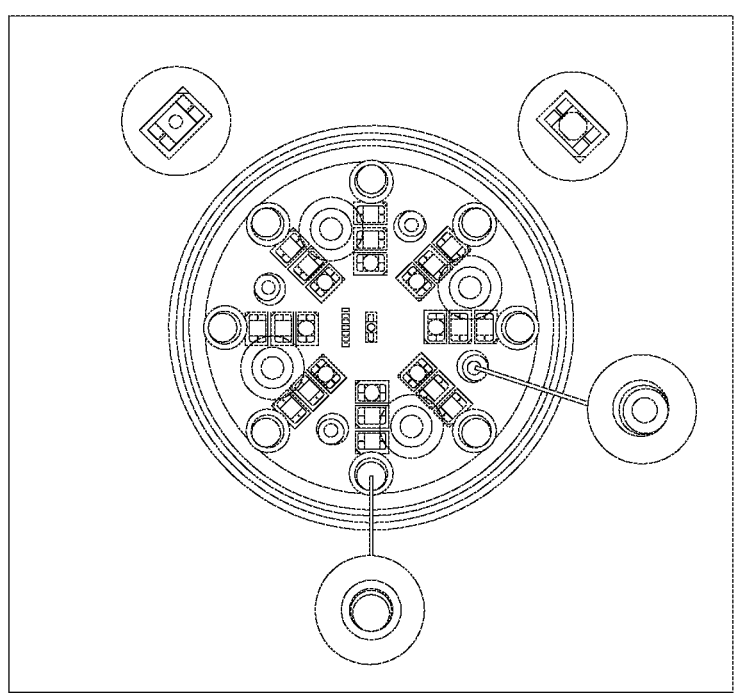
FIG. 5 is a photograph with components enlarged of the light delivery surface of the MR5Active Pro LaserShower device of FIG. 5.

The photoceutical medical device 102 can include a circuit board 202 (also referred to as a printed circuit board), which can hold the light sources (which can be positioned in a manner for delivery, as shown, for example, in FIG. 5, but this is not the exclusive manner of delivery). Each light source can deliver a unique signal from a unique position, and these unique signals are combined to form the photoceutical. The light sources can include one or more superpulsed lasers, one or more red light emitting diodes (LEDs), and/or one or more infrared light emitting diodes (IRED). In some instances, the circuit board can include one or more magnetic sources. The light sources (and magnetic sources, in some instances) can be arranged in configurations including a single source, a group of multiple sources, and/or specific cluster of sources.

The circuit board can be, in some instances, a flexible circuit board, and in other instances a rigid circuit board. The circuit board 202 can be connected to a controller 204 and a power source 206. The controller 204 can be configured to receive an input, for example an external input from a user, a memory storing instructions, and a processor to execute the instructions. The instructions can include programming for delivery of the photoceutical 204, including the duration of the delivery of the photoceutical, the start time, the stop time, the total power, based on the power delivered by each source (the types of light sources and, in some instances, the magnetic sources), and the like. Although the controller 204 can be controlled by an input, in some instances, the controller 204 can be preprogrammed such that only a start or stop button is required. In some instances, at least a portion of the controller can be external to the photoceutical medical device 102. The power source 206 can provide line power and/or battery power to power at least a portion of the photoceutical delivery device 102 (e.g., the controller 204, which can deliver power to the circuit board 202) and can include additional circuitry related to power delivery. The powers, densities, and intensities can be outputs from 1 mW to 100 W.

Figure 3:
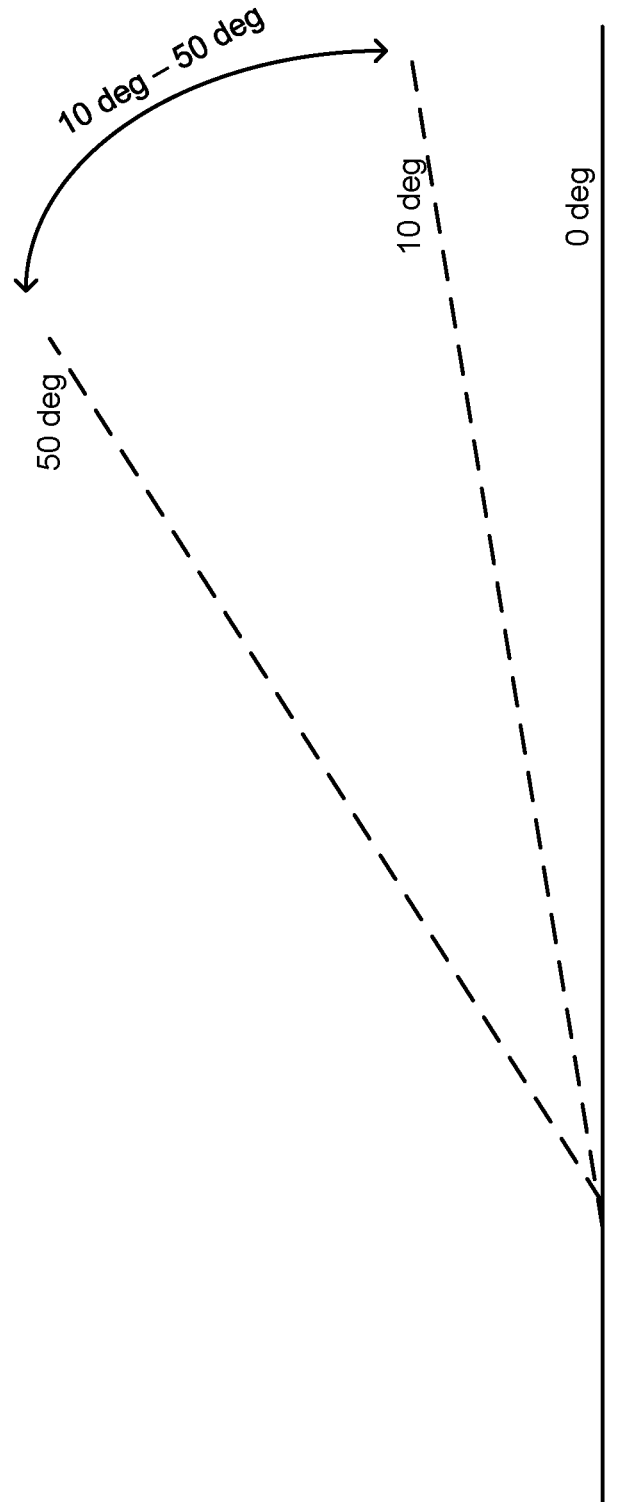
FIG. 3 is a diagram showing an example variable incline of the circuit board of the photoceutical medical device of FIG. 2.

In some instances, the photoceutical medical device 102 can include a motor 208 to incline the circuit board 202 for delivery to at least one of the predefined sites on the patient's body. However, in other instances, the circuit board 202 can be angled manually by angling the photoceutical medical device 102. As shown in FIG. 3, in some instances, like when the photoceutical 104 is delivered to the neck of the patient, the circuit board need not be on an incline (0 deg as shown in FIG. 3). However, when the photoceutical 104 is delivered to one of the sites on the patient's abdomen, the circuit board can be inclined from 10 degrees to 50 degrees (10 deg-50 deg as shown in FIG. 3) to facilitate delivery of the photoceutical 104 to the diaphragm. The incline may be different (but between 10 degrees and 50 degrees) for different sites on the patient's abdomen; in these instances, the photoceutical medical device 102 can be placed at an edge of costal cartilage and angled to facilitate delivery of the photoceutical 104 to the diaphragm. The motor 208 can be programmed to move the circuit board to a specific include to deliver the photoceutical 204 based on the anatomical location of the predefined site.

Figure 4:
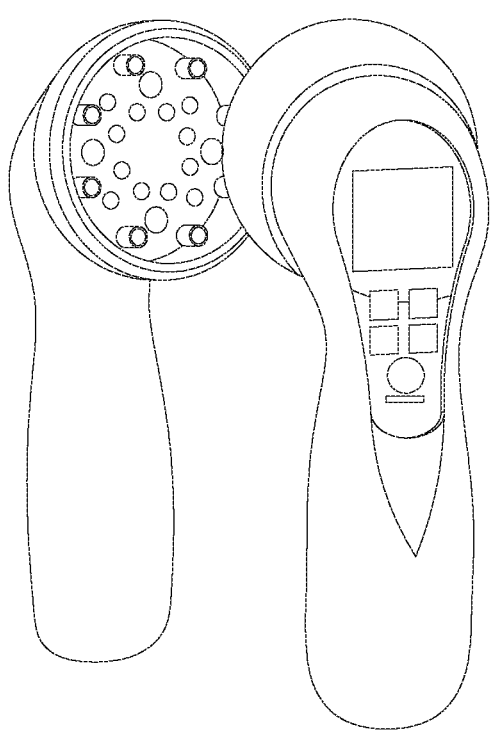
FIG. 4 is a photograph of a MR5Active Pro LaserShower device, an example of the photoceutical medical device of FIG. 1.

FIGS. 4 and 5 show an MR5Active Pro LaserShower, 250 Hz frequency; MultiRadiance Medical of Solon, Ohio, which is one example of a photoceutical medical device 102. The MR5Active Pro LaserShower may not include the motor 208, but can be physically angled at the different positions. The MR5Active Pro LaserShower can deliver the photoceutical including the application of a specific combination of infrared super pulsed laser (SPL) light, infrared IRED light, red LED light, and a static magnetic field (parameters shown in Table 1). As shown in FIG. 4, the MR5Active Pro LaserShower includes a plurality of buttons that allow a user to control application of the photoceutical, including on/off and start/stop. The controls may be available for other features, as well, such as defining the photoceutical and/or controlling the delivery time.

TABLE 1

Parameters for a specific application of the photoceutical using an MR5Active Pro LaserShower (FIGS. 4 and 5), 250 Hz frequency; MultiRadiance Medical of Solon, Ohio.

| Wavelength | Source | Number of Sources | Power/each | Total Power | |
|---|---|---|---|---|---|
| 905 nm | SPL | 4 | 50 W | 0.08-80 | mW |
| 850 nm | IRED | 8 | 37.5 mW | 300 | mW |
| 630 nm | LED | 8 | 25 mW | 200 | mW |
| n/a | MAGNET | 8 | 13 mT | 110 | mT |

Figure 6:
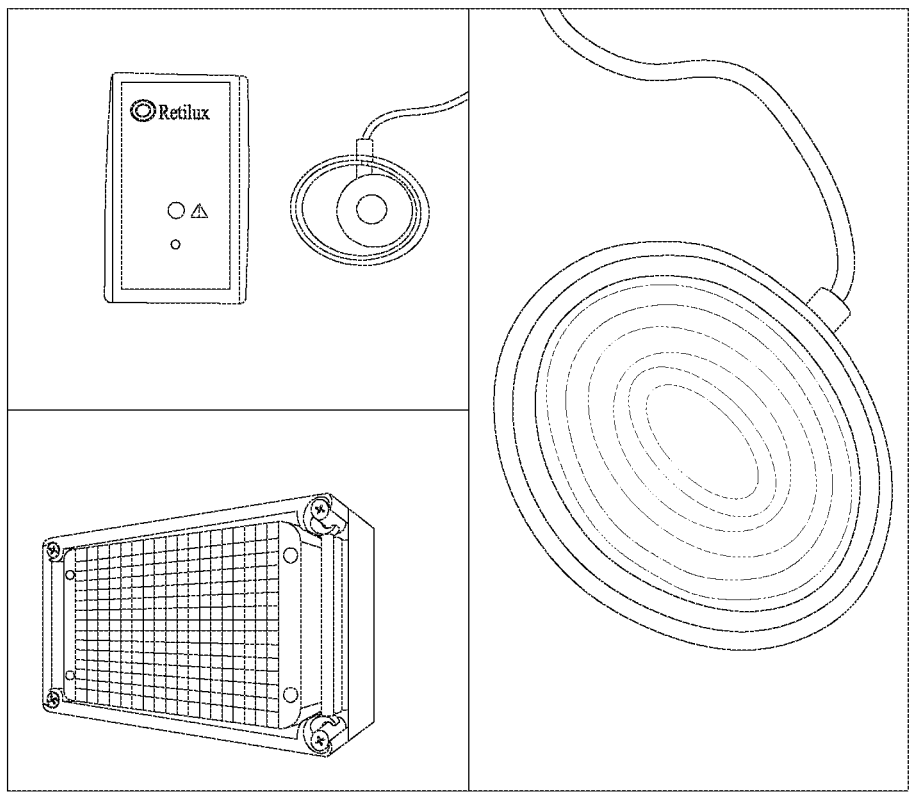
FIG. 6 shows three alternative examples of the photoceutical medical device of FIG. 1.

FIG. 6 shows additional examples of devices from MultiRadiance Medical of Solon, Ohio that can be used as photoceutical medical device 102 that can be used to deliver the light signal of a single wavelength, of multiple wavelengths and in some instances can include magnets (under a range of parameters).

Any of the examples of FIGS. 4, 5, and 6 can include additional components (e.g., a new chassis or a modified existing chassis) that can allow the circuit board 202 to be inclined like FIG. 3. In each case, the inclination can be manual and/or hands-free automatic. Additionally or alternatively, any of the examples of FIGS. 4, 5, and 6 can include software programmed to manipulate the inclination and/or the dosage.

As noted above, sites can be chosen from any of the locations shown in the black boxes in FIGS. 7-9. The figures are not mutually exclusive. Please also note that the sites may be chosen anywhere in the boxes and that the sites can extend beyond the bounds of the boxes.

Figure 10:
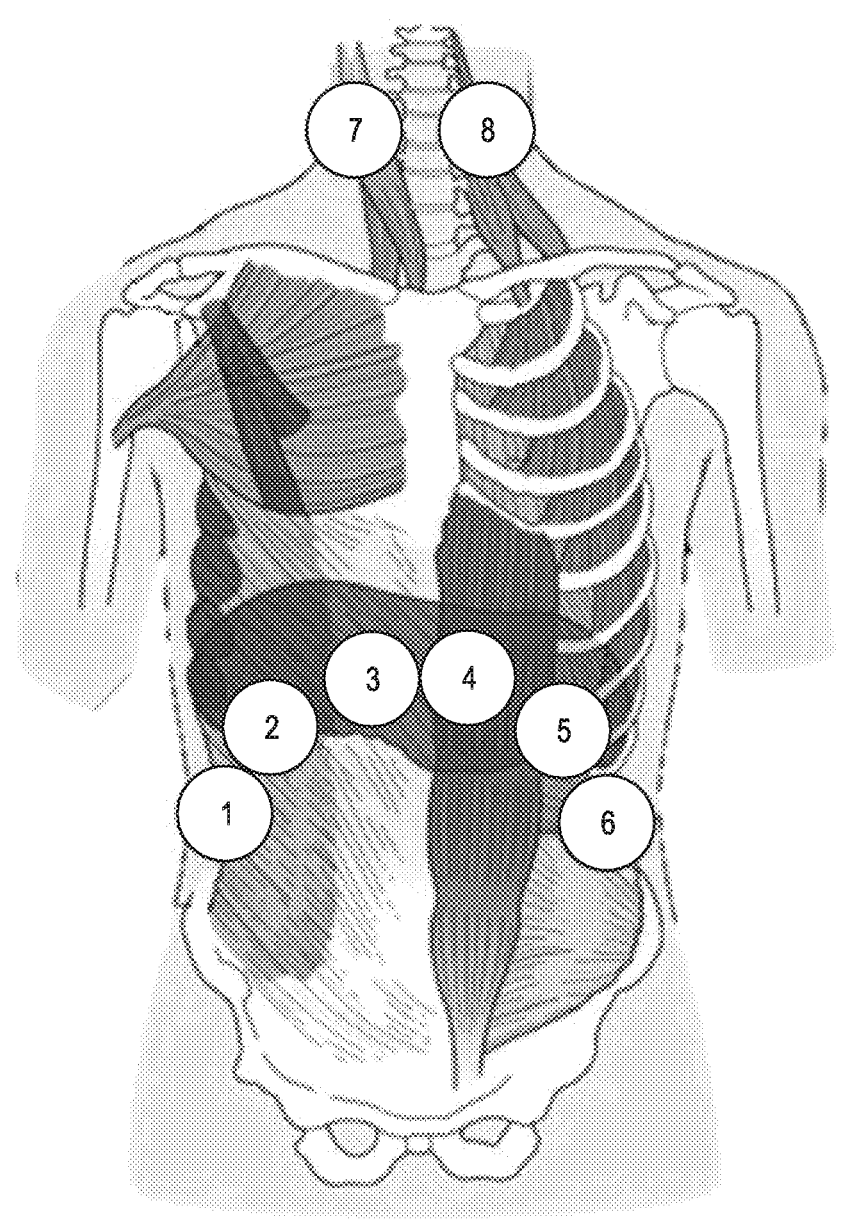
FIGS. 10-11 are diagrams of a patient's inspiratory musculature and examples of eight sites that can be used for delivery of the photoceutical.
Figure 11:
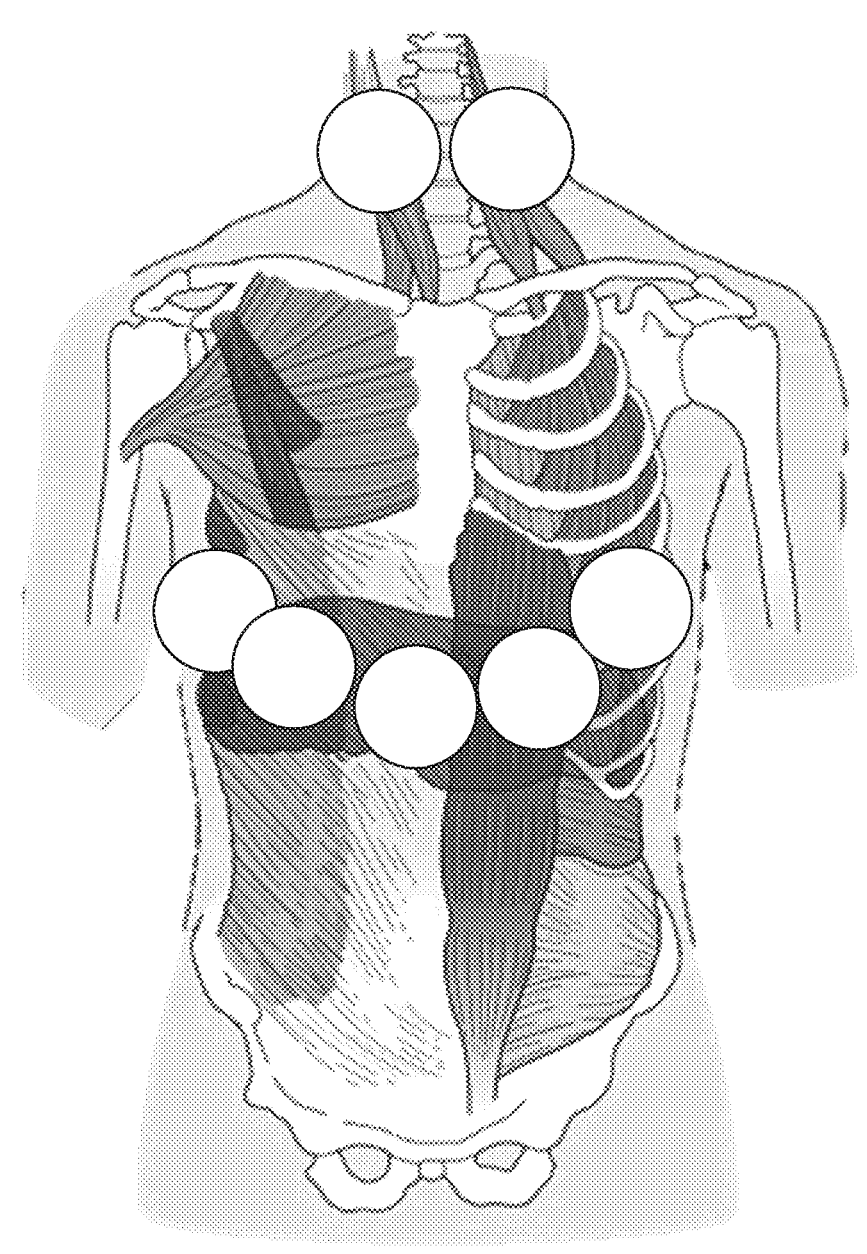

An example of the sites that can be chosen are shown in FIGS. 10 and 11. The sites on the diaphragm (chosen from FIG. 7) can be either on an upward slope from the previous site (FIG. 11) or a downward slope from the previous site (FIG. 10) (in other words, FIG. 10 is a downward facing parabola, while FIG. 11 is an upward facing parabola).

Figure 12:
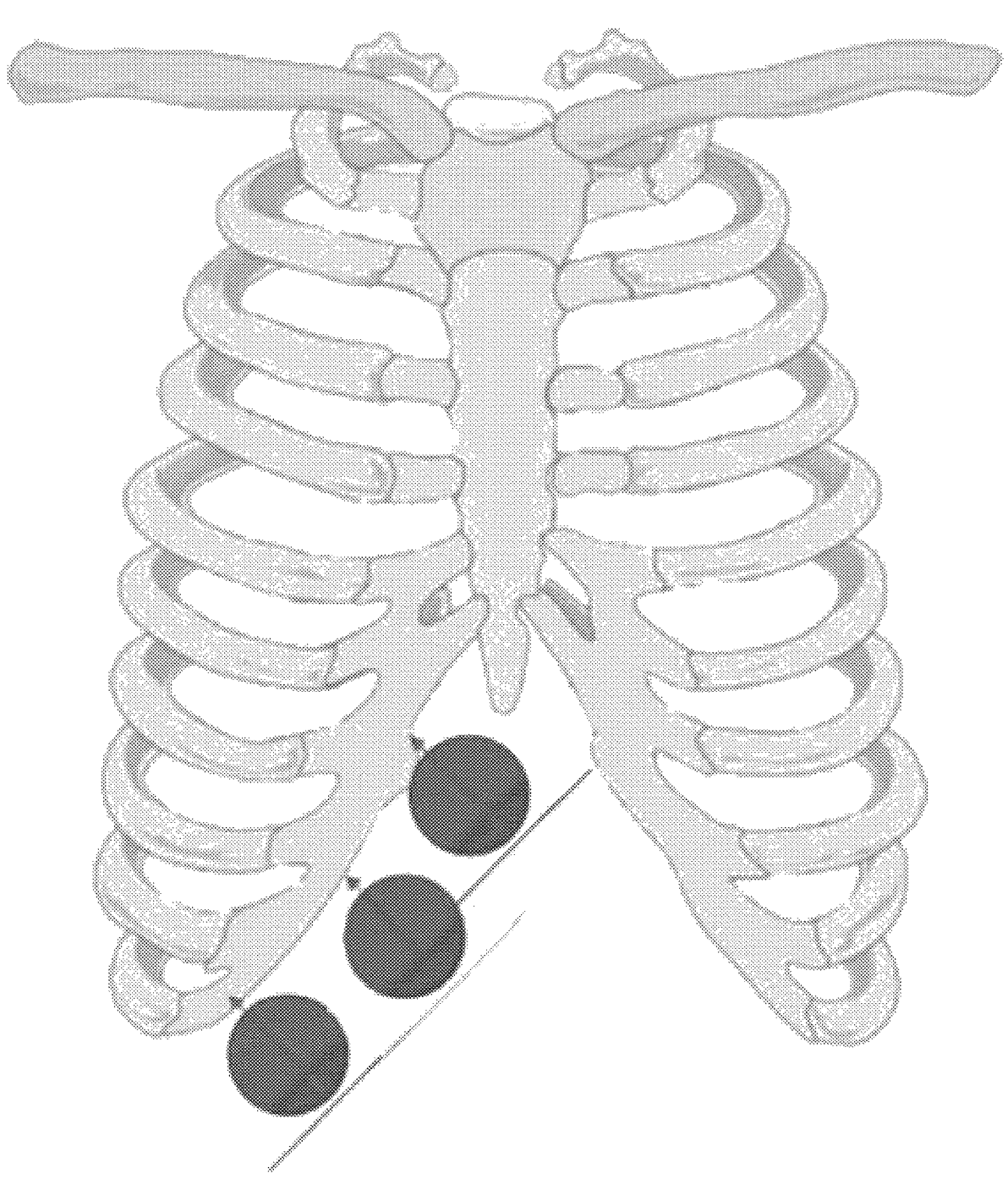
FIG. 12 is a diagram of a portion of the eight locations for delivery of the photoceutical showing how the photoceutical medical device is angled to deliver the photoceutical to the patient's diaphragm.

Using FIG. 10 as an example, the first 6 sites cover the abdomen and numbered in sequence from 1-6 to treat the diaphragm. The diaphragm is recessed under the ribcage, so the light aperture of the photoceutical delivery device (e.g., the MR5Active Pro LaserShower of FIGS. 4-5) must be angled (from 10 degrees to 50 degrees) by depressing the edge furthest from the costal cartilage into the abdominal wall (FIG. 12) to improve delivery of the light energy to the muscle. The angle allowed light to be directed under the ribcage at the left or right domes of the diaphragm. Pressure on the xiphoid process (the cartilaginous section at the lower end of the sternum, which is not attached to any ribs, and gradually ossifies during adult life) was avoided for all sites because pressure can cause the xiphoid process to break off, resulting in punctures of the diaphragm or even the liver.

In FIG. 10, the edge of the light aperture of the MR5Active Pro LaserShower that forms a perpendicular angle and is the farthest away from the costal cartilage landmark (bottom area of circle) can be depressed at the angles noted below, for example.

- a. Location 1: right $10^{th}$ rib at the costal cartilage junction, aperture angle 30 deg
- b. Location 2: right $8^{th}$ rib at the costal cartilage junction, aperture angle 20 deg
- c. Location 3: right $7^{th}$ rib at the costal cartilage junction, aperture angle 10 deg
- d. Location 4: left $10^{th}$ rib at the costal cartilage junction, aperture angle 30 deg
- e. Location 5: left $8^{th}$ rib at the costal cartilage junction, aperture angle 20 deg
- f. Location 6: left $7^{th}$ rib at the costal cartilage junction, aperture angle 10 deg The final two sites in FIG. 10 cover the neck, labeled in sequence 7 and 8. Site 7 was at the right body of the sternocleidomastoid, while site 8 was at the left body of the sternocleidomastoid. The light aperture of the photoceutical delivery device (e.g., the MR5Active Pro LaserShower of FIGS. 4-5) need not be angled for delivery of the dose to sites 7 and 8.

V. Methods

Figure 13:
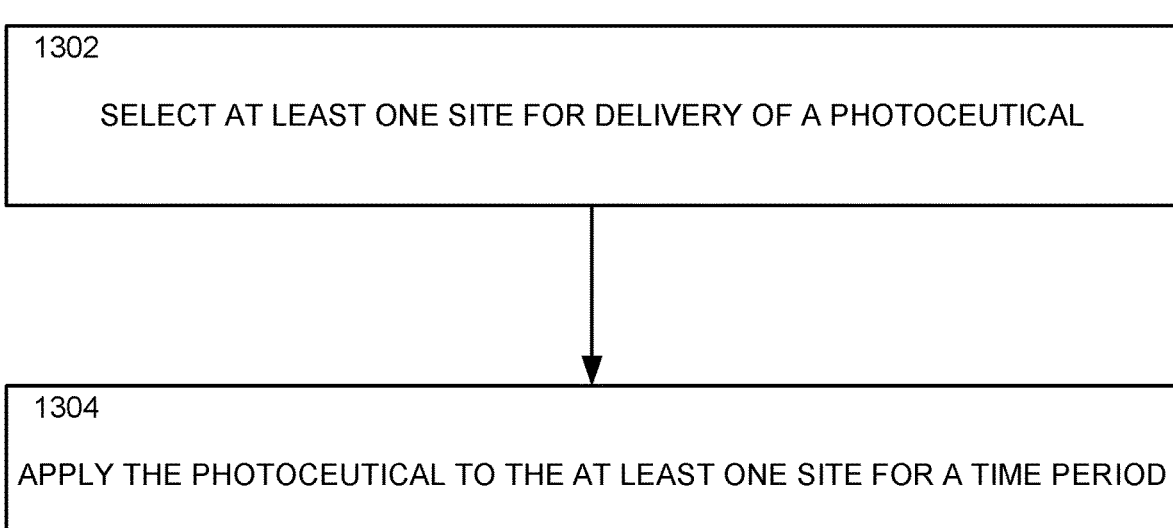
FIGS. 13-14 are process flow diagrams showing an example of a method for delivering a photoceutical to at least one predefined location on the body of a patient at risk of or suffering from respiratory insufficiency in accordance with an aspect of the present disclosure.
Figure 14:
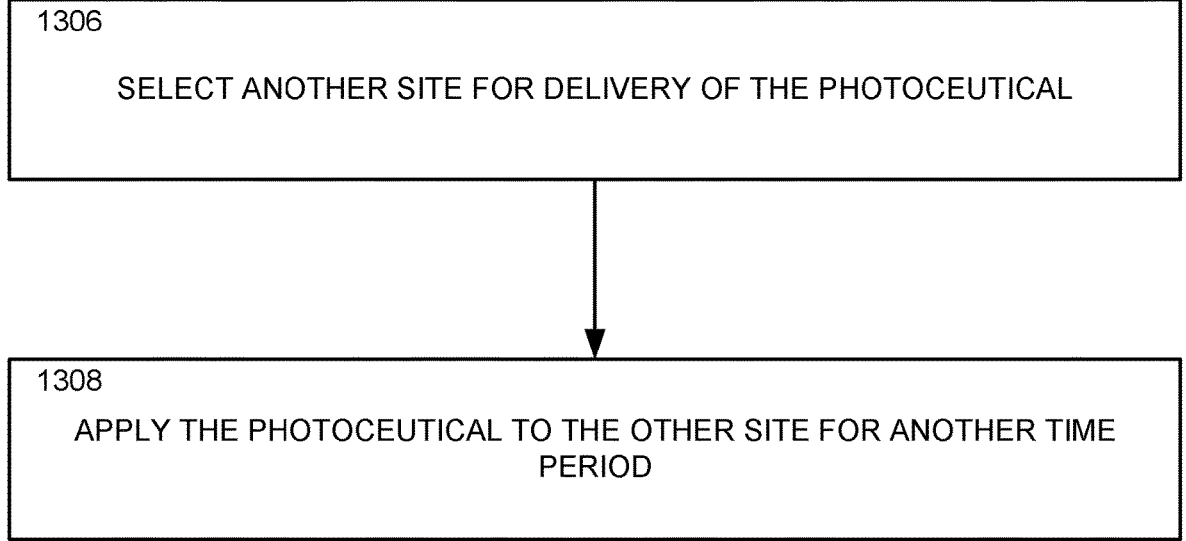

Another aspect of the present disclosure can include a method, as shown in FIGS. 13 and 14, for treating a patient at risk of or suffering from respiratory insufficiency with a photoceutical delivered by a photoceutical medical device. The photoceutical can be delivered to a patient (e.g., the photoceutical can be configured with one or more parameters) to help the patient achieve goals at various medical stages. For example, delivery of the photoceutical can be used to protect the patient (e.g., before a ventilator is applied) with the goal of helping to reduce the risk of using/requiring a ventilator. As another example, the photoceutical can be delivered during ventilation (e.g., using a ventilator) with the goal of reducing diaphragm dysfunction (during or after ventilation, making it easier to remove the patient from the ventilator). As a further example, the photoceutical can be used after discharge (e.g., from a medical facility) with the goal of improving respiratory function and recovery. In yet another example, the photoceutical can be used after ventilation (e.g., after a patient has been removed from a ventilator) with the goal of improving respiratory function. Additional uses/protections are possible. The delivery can be before hospitalization, during hospitalization, and/or after hospitalization. The deliver can be used without requiring hospitalization (e.g., as a treatment).

The methods can be executed by hardware—for example, at least a portion of the system 100 (the photoceutical delivery device 102) shown in FIGS. 1 and 2 and described above. The methods are illustrated as process flow diagrams with flowchart illustrations. For purposes of simplicity, the methods are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods. Additionally, one or more elements that implement the methods, such as the photoceutical delivery device 102 or the controller 204 of FIG. 2, may include a nontransitory memory and one or more processors that can facilitate the configuration and generation of the light of the photoceutical.

At step 1302, at least one site on a body of a patient at risk of or suffering from respiratory insufficiency can be selected for delivery of a photoceutical (a light signal or light signal+magnetic signal described with respect to the Systems). The site can be any site at least partially within the black boxes shown in FIGS. 7-9.

At step 1304 a dose of the photoceutical can be delivered at the site through a photoceutical medical device 102 for a time period. The photoceutical medical device 102 can be a handheld device (e.g., a probe), as shown in FIG. 1, or it can be applied to the patient's body independently (without being handheld, such as a pad or a flexible device). For example. the photoceutical device may comprises at least one super pulsed laser that can provide superpulsed light of a first wavelength, at least two non-coherent light sources that can provide light of a second wavelength, and at least two other non-coherent light sources to provide light of a third wavelength. The light signal delivered by the photoceutical medical device can include a combination of superpulsed light of the first wavelength, light of the second wavelength, and light of the third wavelength. For example, the first wavelength can be between 850 nm and 950 nm, the second wavelength can be between 800 nm and 900 nm, and the third wavelength can be between 580 and 800 nm. The photoceutical medical device can also comprise at least two magnetic sources to provide a magnetic signal. The magnetic sources can be, for example, one or more of: a permanent magnet, a temporary magnet, and an electromagnet.

In another aspect the photoceutical medical device can comprise at least four super pulsed lasers, at least eight light sources, at least eight other light sources, and at least eight magnetic sources. The at least four super pulsed lasers can each provide the superpulsed light of the first wavelength. The at least eight light sources can each provide the light of the second wavelength. The at least eight other light sources can each provide the light of the third wavelength. The at least eight magnetic sources can provide a magnetic signal.

The dose of the light signal delivered to the site by the photoceutical medical device can be delivered for a first time period from a first start to a first end time. The first time period can be between 30 seconds and 300 seconds. The dose delivered for the first time period can be a value between 3 J and 2000 J, for example, 31.5 J. When the site is on an abdomen of the patient to target the diaphragm the delivering the light signal can further include angling at least a portion of the photoceutical medical device (e.g., at least the circuit board) so that the light signal enters the body of the patient at an angle from 10 degrees to 50 degrees to reach the diaphragm of the patient. However, the photoceutical medical device need not be inclined to deliver the photoceutical to any sites being on the neck or on the chest of the patient.

Referring now to FIG. 14, the method continues at step 1306 when another site is selected (can be any site at least partially within the boxes of FIGS. 7-9) and the photoceutical medical device 102 is moved to another site and, at step 1308, a dose of the light signal is delivered to the other site through the photoceutical medical device for another time period. The photoceutical medical device can be moved to the other of the at least two sites after the first end time and the other dose of the light signal can be delivered at the another of the at least two sites for another time period from a second start time to a second end time. The other time period can be between 30 seconds and 300 seconds.

VI. Experimental

The following experiment shows the efficacy of the use of multi-wavelength photobiomodulation therapy+static magnetic field (PBMT-sMF) for peripheral oxygen saturation, pulmonary function, massive lung damage, and fibrosis as a pulmonary complication after COVID-19.

A 53-year-old Mexican man who presented with decreased peripheral oxygen saturation, massive lung damage, and fibrosis after COVID-19 received PBMT-sMF treatment once a day for 45 days. The treatment was irradiated at six sites in the lower thorax and upper abdominal cavity and two sites in the neck area. The patient was able to leave the oxygen support during the treatment and increase his peripheral oxygen saturation. In addition, the patient showed improvements in pulmonary severity scores and radiological findings. Finally, the patient presented with normal respiratory mechanics parameters in the medium-term, indicating total pulmonary recovery. The use of PBMT-sMF leads to safe treatment of and recovery from pulmonary complications after COVID-19, with regard to the structural and functional aspects.

Case Report

A 53-year-old Mexican man, who was overweight and had a history of serological antibody tests for toxocariasis positive, brucellosis, gout, conjunctivitis, rhinitis, seasonal allergies, sneezing, and nasal congestion, presented with generalized pain, fatigue, intermittent fever (38.5-40° C.), dry cough, and dyspnea. SARS-CoV-2 diagnosis was confirmed by reverse transcription polymerase chain reaction (RT-PCR) using a nasopharyngeal swab. The patient was admitted to the hospital with an $SpO_2$ of 74% and oxygen support of 14 L/min. Chest radiography demonstrated massive lung damage and fibrosis caused by severe pneumonia. At the hospital, the patient was treated with ceftriaxone and prednisone, along with enoxaparin injections and oral aspirin. After 10 days at the hospital, the patient improved, and he was discharged from the hospital. However, the patient still presented with generalized fatigue, and oxygen support (2 L/min) was still required for sleeping and eating. Therefore, ten days after discharge from the hospital, the patient sought complementary treatment with PBMT-sMF to improve his health status.

Pretreatment Clinical Findings

The patient's response to the PBMT-sMF treatment was evaluated by monitoring $SpO_2$ from the time of admission to the hospital (baseline), until discharge from the hospital, 10 days after the start of treatment, immediately after the end of the treatment, and 4 months after the end of the treatment with PBMT-sMF. In addition, we evaluated the progression of the imaging findings in the chest X-ray from the first X-ray at baseline, until 10 days after the start of the treatment, and 4 months after the end of the treatment with PBMT-sMF. Finally, to quantify the extent of SARS-CoV-2 infection in the lungs, the severity score was calculated from chest X-rays. The adapted and simplified Radiographic Assessment of Lung Edema (RALE) score was used. A score ranging from 0 to 4 was assigned to each lung based on the extent of consolidation or ground glass opacity: 0, no involvement; 1, <25% involvement; 2, 25-50% involvement; 3, 50-75% involvement; and 4, >75% involvement. The final severity score was calculated as the sum of the scores for each lung. The RALE score was calculated at baseline, 10 days after the start of treatment, and 4 months after the end of the treatment with PBMT-sMF.

Intervention

Ten days after discharge from the hospital, the patient started the multi-wavelength PBMT-sMF treatment. PBMT-sMF was irradiated using a cordless, portable MR5 Laser-Shower™ device (Multi-Radiance Medical™, Solon, Ohio, USA). Six sites in the lower thorax/upper abdominal cavity were irradiated in addition to two sites in the neck area (FIG. 10). At each treatment session, the patient received a total of 31.50 J per irradiated site. The treatment time per site was 60 s, yielding 480 s per treatment session. The treatment was performed once daily for 45 days. The dose and irradiation sites were established based on previous studies. Table 1 describes the PBMT-sMF parameters.

TABLE 1

Full description of the PBMT-sMF parameters.

| | Lower Thorax/ upper Abdominal Cavity | Neck Area |
|---|---|---|
| Number of lasers | 4 | 4 |
| Wavelength (nm) | 905 | 905 |
| Frequency (Hz) | 250 | 250 |
| Peak power (W)-each | 50 | 50 |
| Average mean optical output (mW)-each | 1.25 | 1.25 |
| Power density (mW/cm$^2$)-each | 3.91 | 3.91 |
| Energy density (J/cm$^2$)-each | 0.234 | 0.234 |
| Dose (J)-each | 0.075 | 0.075 |
| Spot size of laser (cm$^2$)-each | 0.32 | 0.32 |
| Number of red LEDs | 8 | 8 |
| Wavelength of red LEDs (nm) | 633 | 633 |
| Frequency (Hz) | 2 | 2 |
| Average optical output (mW)-each | 25 | 25 |
| Power density (mW/cm$^2$)-each | 29.41 | 29.41 |
| Energy density (J/cm$^2$)-each | 1.765 | 1.765 |
| Dose (J)-each | 1.50 | 1.50 |
| Spot size of red LED (cm$^2$)-each | 0.85 | 0.85 |
| Number of infrared LEDs | 8 | 8 |
| Wavelength of infrared LEDs (nm) | 850 | 850 |
| Frequency (Hz) | 250 | 250 |
| Average optical output (mW)-each | 40 | 40 |
| Power density (mW/cm$^2$)-each | 71.23 | 71.23 |
| Energy density (J/cm$^2$)-each | 4.286 | 4.286 |
| Dose (J)-each | 2.40 | 2.40 |
| Spot size of infrared LED (cm$^2$)-each | 0.56 | 0.56 |
| Magnetic field (mT) | 110 | 110 |

TABLE 1-continued

Full description of the PBMT-sMF parameters.

| | Lower Thorax/ upper Abdominal Cavity | Neck Area |
|---|---|---|
| Irradiation time per site (sec) | 60 | 60 |
| Number of irradiated sites | 6 | 1 (bilaterally) |
| Total dose delivered to the muscle group (J) | 189.00 | 31.50 (bilaterally) |
| Aperture of device (cm$^2$) | 33 | 33 |
| Application mode | Cluster probe held stationary in skin contact with a 90-degree angle and slight pressure | Cluster probe held stationary in skin contact with a 90-degree angle and slight pressure |

Post-Treatment Outcomes

After 10 days of PBMT-sMF treatment, the SpO$_2$ of the patient increased from 89% to 93% at 2 L/min oxygen. After 40 days of treatment with PBMT-sMF, the patient was able to leave the oxygen support. After 45 days, at the end of treatment with PBMT-sMF, the patient's SpO$_2$ was at 96-98%. Finally, in the last evaluation, 4 months after PBMT-sMF treatment, the patient's SpO$_2$ was at 98% (Table 2).

Figure 15:
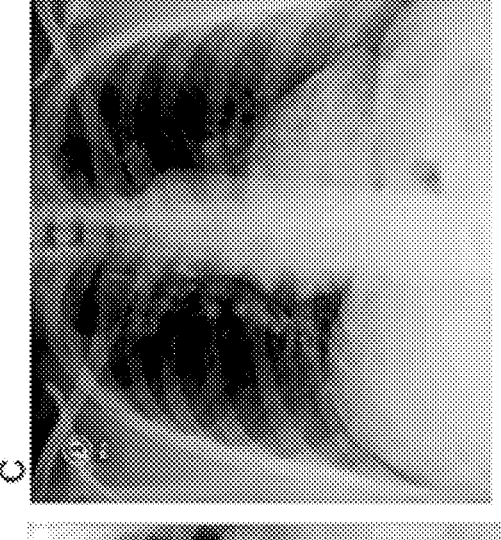
FIG. 15 shows recovery of a patient's lungs after COVID-19 aided by PBMT.
Figure 15:
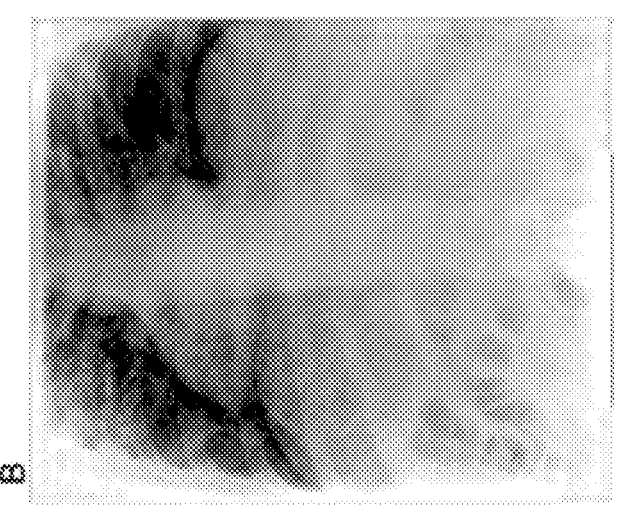
Figure 15:
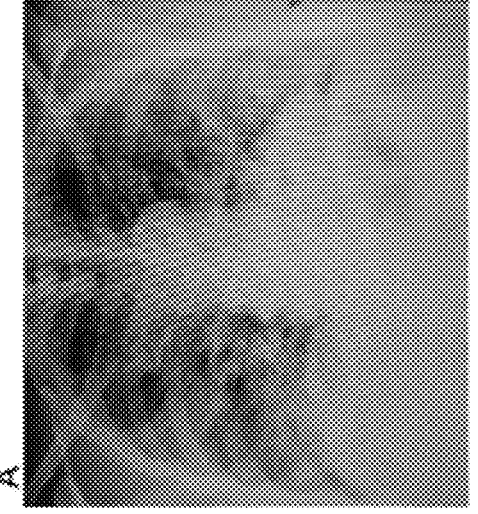

FIG. 15 shows the extent of SARS-CoV-2 infection in the lungs. In addition, this was the basis for measuring the RALE score. When the patient was admitted to the hospital, his RALE score was 7 (FIG. 15, element A). However, on the second chest radiograph, his RALE score worsened to 8 (FIG. 15, element B). Finally, on the last radiograph, at 4 months follow-up evaluation, his RALE score was 0, indicating total recovery of the lungs (FIG. 15, element C) (Table 2).

TABLE 2

Post-treatment outcomes.

| Variables. | Baseline | Discharge from Hospital | 10 Days of PBMT-sMF | After End of Treatment | 4 Months Follow-Up |
|---|---|---|---|---|---|
| SpO$_2$ (%) | 74 | 89 | 93 | 96-98 | 98 |
| RALE | 7 | — | 8 | — | 0 |

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:

selecting at least six sites on a body of a patient for delivery of a photoceutical to at least one primary inspiratory muscle and/or a lung of the patient by a photoceutical medical device, wherein at least one site is on an abdomen of the patient and at least one site is on a neck of the patient, wherein the photoceutical comprises light of at least one wavelength; and applying the photoceutical at the at least one site on the body of the patient by the photoceutical medical device for a time period from a first start time to a first end time to treat the at least one primary inspiratory muscle and/or the lung of the patient to preserve and/or enhance a respiratory function of the patient wherein the applying further comprises placing the photoceutical medical device at the at least one site on the abdomen of the patient at an edge of the costal cartilage of the patient while avoiding the xiphoid process of the patient.

2. The method of claim 1, wherein the wavelength is from 600 nm to 1200 nm.

3. The method of claim 1, wherein the photoceutical comprises at least three light signals, each having a wavelength chosen between 600 nm and 1200 nm.

4. The method of claim 1, wherein the photoceutical comprises at least one of superpulsed light of a first wavelength, pulsed light of a second wavelength, and/or continuous light of a third wavelength.

5. The method of claim 1, wherein the photoceutical comprises superpulsed light of a first wavelength, pulsed and/or continuous light of a second wavelength, and a pulsed and/or continuous light of a third wavelength.

6. The method of claim 5, wherein the photoceutical medical device comprises:

at least one superpulsed laser to provide the superpulsed light of the first wavelength, at least two non-coherent light sources to provide the pulsed and/or continuous light of the second wavelength, and at least two other non-coherent light sources to provide the pulsed and/or continuous light of the third wavelength.

7. The method of claim 6, wherein the photoceutical medical device further comprises at least two magnetic sources to provide a magnetic signal, wherein the photoceutical further comprises the magnetic signal.

8. The method of claim 5, wherein the photoceutical medical device comprises:

at least four superpulsed lasers, each configured to provide the superpulsed light of the first wavelength;

at least eight non-coherent light sources, each configured to provide the pulsed and/or continuous light of the second wavelength;

at least eight other non-coherent light sources, each configured to provide the pulsed and/or continuous light of the third wavelength; and at least eight magnetic sources to provide a magnetic signal, wherein the photoceutical comprises the superpulsed light of the first wavelength, the pulsed and/or continuous light of the second wavelength, the pulsed and/or continuous light of the third wavelength, and the magnetic signal.

9. The method of claim 5, wherein the first wavelength is between 850 nm and 950 nm, the second wavelength is between 800 nm and 900 nm, and the third wavelength is between 580 nm and 800 nm.

10. The method of claim 1, wherein the patient suffers from COVID-19, Duchenne muscular dystrophy (DMD), pneumonia, tuberculosis, sarcoidosis, idiopathic pulmonary fibrosis, interstitial lung disease, lung cancer, pulmonary fibrosis, rheumatoid arthritis, infant respiratory distress syndrome, acute respiratory distress syndrome, inflammatory bowel disease, systemic lupus, asthma, chronic bronchitis, emphysema, cystic fibrosis, pleural effusion, and/or chronic obstructive pulmonary disease (COPD).

11. The method of claim 1, wherein the selecting further comprises selecting at least two sites on the body of the patient for delivery of the photoceutical to the at least one primary inspiratory muscle of the patient and/or the other lung of the patient.

12. The method of claim 11, wherein at least one site is on an abdomen of the patient and at least one site is on a neck of the patient.

13. The method of claim 1, wherein the time period comprises from 30 seconds to 1 hour.

* * * * *